United States Patent [19]

Conklin

[11] Patent Number: 5,158,530
[45] Date of Patent: Oct. 27, 1992

[54] ORTHOPEDIC CASTING METHOD

[75] Inventor: Jonathan R. Conklin, East Greenwich, R.I.

[73] Assignee: Wardwell Braiding Machine Company, Central Falls, R.I.

[21] Appl. No.: 801,660

[22] Filed: Dec. 9, 1991

[51] Int. Cl.⁵ ............................................. A61F 13/04
[52] U.S. Cl. .......................................... 602/8; 602/44; 602/76; 602/900; 602/901
[58] Field of Search ................. 602/901, 900, 60, 62, 602/63, 1, 5-8, 75, 76

[56] References Cited

U.S. PATENT DOCUMENTS 2,739,587  3/1956  Scholl .................................. 602/1
4,800,872  1/1989  Buese et al. ........................... 602/8
5,016,622  5/1991  Norvell ................................. 602/7

Primary Examiner—Robert A. Hafer
Assistant Examiner—Kevin G. Rooney
Attorney, Agent, or Firm—Salter, Michaelson & Benson

[57] ABSTRACT

A method of applying an orthopedic cast to an injured body portion consisting of braiding a tubular cast, in situ, around the injured body portion. A somewhat modified conventional braiding machine is operative for applying the tubular braid of fibrous casting yarns around the injured body portion, to form a braided cast which conforms to the shape of the injured body portion. The braided cast is then coated with a matrix material, which provides the necessary rigidity to the cast, yet allows the cast to breathe.

12 Claims, 2 Drawing Sheets

ORTHOPEDIC CASTING METHOD

BACKGROUND OF THE INVENTION

The present invention relates to orthopedic casting methods, and more specifically relates to a method of applying an orthopedic cast by braiding fibrous casting yarns, in situ, around an injured body portion.

Traumatic injuries to body portions, particularly a fracture of a bone or damage to soft tissues, are frequently treated by immobilizing the injured body portion with a rigid cast. Heretofore, the application of medical casting materials required a labor intensive process of manually wrapping the injured limb with rolled strips of a tape-like plaster or fiberglass mesh fabric. The desired cast geometry for the type of body portion involved was achieved by wrapping, stretching, twisting, and layering, the rolls of plaster or fiberglass fabric over and around the injured body portion. In general, manual application of conventional casting fabrics is a lengthy and complicated procedure which requires a significant amount of skill and training, and many hospital personnel are required to dedicate a substantial portion of their medical training toward learning casting procedures. Although the conventional casting methods produce casts which have the rigidity and durability necessary for immobilizing injured body portion for extended periods of time, there are several disadvantages which are apparent. Because the rolls of casting fabric are manually applied in irregular, wrapped geometries, the amount of casting fabric utilized is much greater than is actually necessary and thus the casts are thick and heavy, and are burdensome and inconvenient to the wearer. Even further, the strips of casting fabric have exposed edges which often fray after hardening of the cast. The frayed edges cause portions of the cast to unravel, and therefore many casts must be replaced periodically. Another problem encountered because of the wrapping and layering procedure is that the several layers of the cast sometimes do not adequately adhere to one another. If the casting material is not applied quickly enough the impregnated matrix material can prematurely set and harden before the cast is completed, and thus, the layers of wrapped casting material do not correctly bond together. It can therefore be seen that the prior art casting methods are inadequate in these regards.

SUMMARY OF THE INVENTION

The instant invention overcomes the problems associated with the prior art casting techniques by providing a novel method of applying a cast to an injured body portion in which fibrous casting yarns are braided in a tubular architecture, in situ, over and around the injured body portion. The braided cast closely conforms to the shape of the injured body portion, thus providing a better fitting cast, and because of the inherent strength of interlocking braided materials, the braiding method reduces the amount of casting material necessary, thus making the cast lighter, and more comfortable for the wearer, as well as easier and more comfortable to the patient when being applied.

Briefly, the casting method comprises applying a protective stocking over the injured body portion, braiding a plurality of fibrous casting yarns in a layered, tubular configuration, in situ, over and around the stocking and injured body portion, thus forming a braided cast, and thereafter coating the braided casting yarns with a resinous matrix material which provides structural rigidity to the outer layers of the braided cast, yet allows the cast to breathe.

The casting yarns are braided around the body portion utilizing a specially adapted composite braiding machine of the so-called "maypole" type which is capable of producing a tubular braided architecture. The braiding machine comprises a base structure having overhead guide rails, a braiding head which is slidingly mounted on the guide rails and which is capable of producing a tubular braid, and a traversing drive motor for traversing the braiding head back and forth the along the guide rails. The braiding head comprises a pair of braiding rings, a plurality of carriers, a plurality of spindles of fibrous casting yarns mounted thereon, and a carrier drive motor.

The casting yarns are braided over and around the injured limb by positioning the injured body portion within the center of the braiding rings, securing the free ends of the casting yarns at one end of the injured body portion, and simultaneously driving the carriers of the braiding head around the body portion, while traversing the braiding head back and forth along the length of the body portion, thereby applying a tubular braided cast around the body portion.

It is therefore an object of the instant invention to provide a novel method of applying a cast to an injured body portion in which fibrous casting yarns are braided, in situ, around the injured body portion.

It is another object of the instant invention to reduce the amount of labor and training skills necessary to apply a cast, by providing a modified braiding machine adapted for automatically braiding casting yarns around an injured body portion.

It is a further object to reduce the discomfort of the patient during the casting of a body portion by providing an automated method which quickly and painlessly braids a cast over the injured body portion.

It is an even further object of the instant invention to provide a lightweight, thin, braided cast, which has the same strength as conventional wrapped casts.

It is a still further object to provide an orthopedic cast which closely conforms, as it is being applied, to the shape of the injured body portion.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 2:
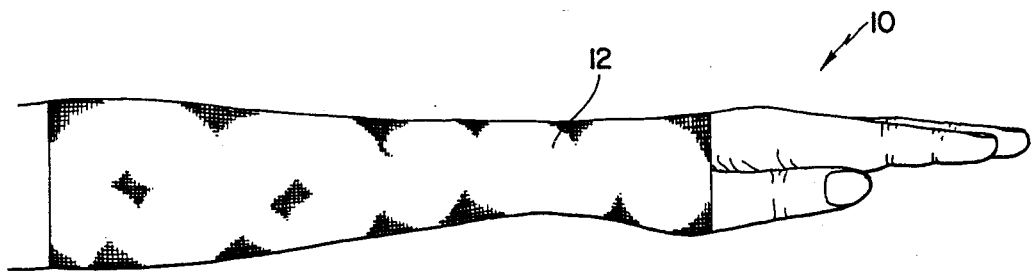
FIG. 2 is a side elevational view of an injured limb having a protective cotton stocking fitted thereon.
Figure 3:
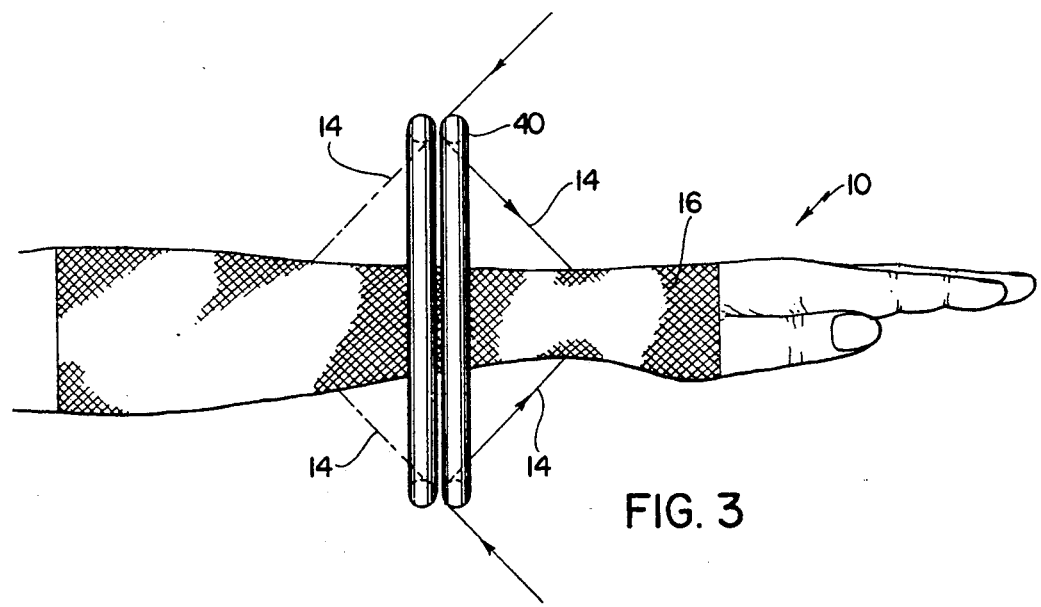
FIG. 3 is a side elevational view of an injured limb as the casting yarn is being applied by the braiding machine.
Figure 4:
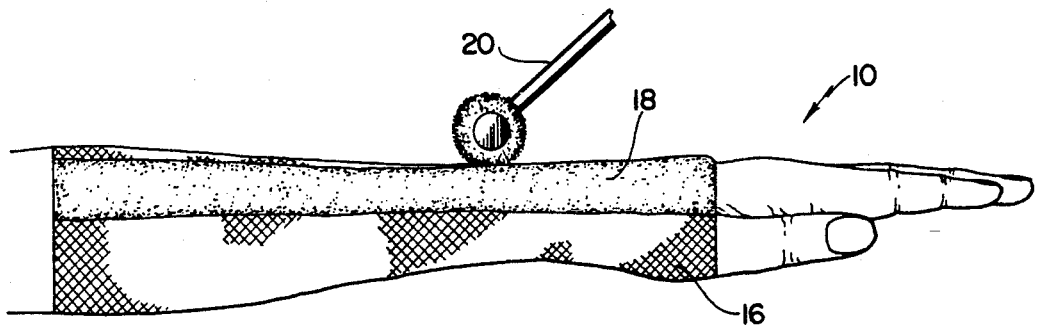
FIG. 4 is a side elevational view of the braided cast having the resinous matrix material being applied thereover.

Referring now to the drawing figures, the steps of the casting method of the instant invention are illustrated and designated in FIGS. 2, 3, and 4. Briefly stated, the casting method of the instant invention comprises braiding a plurality of fibrous casting yarns, in situ, around an injured body portion, such as an arm, which is generally indicated at 10. As seen in FIG. 2., a protective stocking material 12 is placed over the injured arm 10 to provide a comfortable barrier layer between the rigid cast and the skin of the arm, and to prevent chafing of the skin of the arm 10. The protective stocking material is preferably a soft hypo-allergenic material, such as cotton, and also preferably has some degree of elasticity in order to conform to the shape of the injured body portion.

As seen in FIG. 3, a plurality of fibrous casting yarns 14 are then braided in a tubular configuration, in situ, over the protective stocking 12, and around the arm 10, to form a tubular braided cast 16, as may be seen in FIG. 4 The casting yarns 14 are preferably a fiberglass material, and are preferably of a multi-filament construction. Although fiberglass is the material of preference, any one of a number of suitable fibrous yarns may be utilized, such as polyethylene, polypropylene, aramid, nylon, and polyester. Other fibrous yarns which may also be utilized include glass, and carbon-based yarns. In addition, other constructions of yarn may also be utilized, such as multi-filament tow, twisted filament yarn, plied yarn, and twisted staple yarn.

Referring now to FIG. 4, after the casting yarns are braided and the braided cast 16 is complete, a hardening matrix material 18 is applied over the braided yarns 14 to provide rigidity to the cast 16. The matrix material 18 is preferably only applied to the outer layers of the cast, and preferably does not clog the open weave of the braid. The preferred method of application of the matrix material 18 is to roll it on with a roller 20. Rolling allows the matrix material 18 to coat and/or impregnate the fibers of the casting yarn 14, yet does not clog the open weave of the braid so that the cast 16 can breathe. The matrix material 18 is preferably a mixture of 100 parts of "TACTIX 123" resin, and 17 parts hardener. This specific resin will deeply penetrate a few layers in a relatively loose braid, but for a tight braid it must be applied on each layer of braid. Other types of matrix materials can also be utilized, including resins of the thermoset and thermoplastic families, such as polyethylene, polypropylene, acrylic, and polyurethane-based resins. A further alternative matrix material is plaster of paris, however, the plaster matrixes tend to be thicker than the other preferred materials, and tend to clog the open weave of the braided cast, and hinder breatheability.

It is contemplated that casting yarns may soon be available with a pre-impregnated matrix material which can be activated after the casting yarns have been braided. The pre-impregnated casting yarns will eliminate the need for externally applying the matrix material, and will even further simplify medical casting procedures.

Braiding the casting yarns directly around the injured body portion provides a seamless tubular cast architecture, which offers many advantages over the conventional casting methods. The braided cast closely conforms to the shape of the body portion, and only requires a few layers of braiding to provide the same strength as the conventional wrapped casts. The braided casts are therefore much lighter in weight than the wrapped casts, and are also more comfortable for the wearer. The braiding methods used to form the braided cast are extremely flexible, and permit tremendous flexibility for medical professionals in designing custom woven casts for specific medical applications.

As an industrial process, braiding is centuries old. In the formative years of braiding technology, braiding techniques were mostly used in the textile fields to produce yarns, general cordage, rope, macrame, shoe laces, fish netting, and other various types of cords and tapes. Over the years however, braiding technology has ascended into the high-tech revolution, and is changing the way engineers think about material fabrication. Once relegated exclusively to low-tech materials, braiding is fomenting its own quiet revolution—with kevlar, fiber-glass, carbon, and pre-impregnated fibers of all types. Braided materials are now being utilized in a variety of ways, such as from windmill spars to rocket-motor parts, skis to utility poles, and bicycle frames to tennis racquets. Because of its versatility, composite braiding is fast becoming a technology of choice in parts fabrication.

The most significant reason for braiding's ascendance into high technology is its simplicity of structure. A braid is formed by crossing a number of strands diagonally, so that each strand passes alternately over-and-under one or more of the others. Since braiding is a combination of weaving and filament winding, it is the best process for any application requiring uncommon strength and flexibility. Braided fibers are mechanically locked for superior strength, and at the same time, they are better able to withstand twisting, shearing, and impact. Furthermore, because of its woven structure, braiding can deal more effectively with complex surfaces.

Braids can generally be divided into two classes: flat braids, and round braids. Flat braids, which are in the form of a flat strip or tape, can be formed in varying widths, and are made with an odd number of strands. Round braids are formed in a tubular architecture, and can be hollow, such as braided nylon climbing ropes, or can have a central core, such as coaxial television cable, and are formed from an even number of strands. Generally, all commercial braiding processes are now performed by automated braiding machines which quickly and efficiently braid all types of fabrics and cables. Round braids, or tubular braids of the type described in the instant invention, are formed using composite braiding machines which comprise a circular braiding head having a plurality of yarn carriers. The carriers are driven around an undulating track in a circular plate, which forms part of the braiding head weaving the braiding yarns under-and-over each other to form the desired braid. Where a specific cross-section of a hollow circular braid is desired, an elongated mandrel is placed in the center of the braiding head, and the carriers are driven around the mandrel while the braiding head is traversed along the length of the mandrel to form the tubular braid. The braid conforms to the surface shape of the mandrel, and the resulting braid has a cross-section identical to the mandrel.

Figure 1:
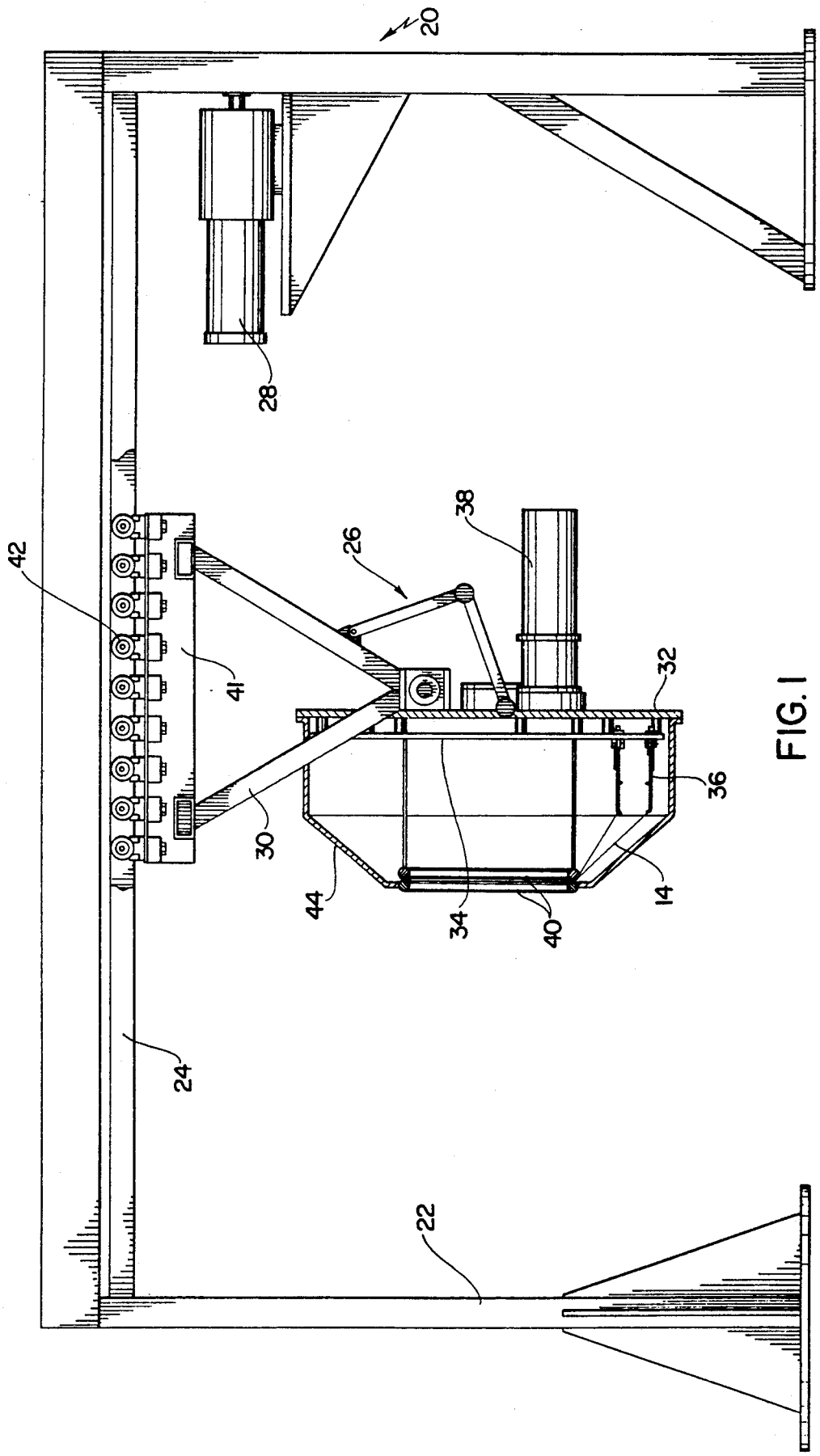
FIG. 1 is a side elevational view of the braiding machine used in carrying out the method of the instant invention.

The braiding step of the instant invention utilizes a slightly modified conventional braiding machine of the "maypole" type to form the tubular braided cast 16, in situ, over-and-around the injured body portion. Referring now to FIG. 1 of the drawing figures, the braiding machine utilized in the present invention is illustrated and generally designated at 20. Briefly, the braiding machine 20 comprises a base structure 22, having overhead guide rails 24, a braiding head generally indicated at 26 which is slidingly mounted on the guide rails 24, and a traversing drive motor 28 for traversing the braiding head back-and-forth along the guide rails 24. The braiding head 26 comprises a support portion 30, a drive plate 32, a track plate 34 having an undulating track (not shown) formed therein, a plurality of spindle carriers 36, a carrier drive motor 38, and a pair of braiding rings 40. The support portion 30 is mounted on a support bracket 41 which is suspended from the guide rails 24 by a plurality of rollers 42, whereupon traversing motor 28 through suitable gearing (not shown) imparts back-and-forth movement to braiding head 26. A plurality of spindles of any suitable casting yarn 14, such as fiberglass, are mounted on the carriers 36, and the free ends of the yarns 14 are fed through the braiding rings 40.

An annular guard member 44 covers the carriers 36 and functions as an acoustical sound enclosure, and also as a protective guard that prevents the patient or clinician from accidentally inserting their hand into the moving carriers. Also, it functions to control the braid angle since the braiding rings are built right into the guard.

Referring back to FIG. 3, the injured body portion 10 can be seen positioned in the center of the braiding rings 40. In effect, the injured body portion replaces the conventional mandrel of conventional tubular braiding machines, and the braiding machine thus applies a braid which conforms to the surface of the injured limb. To apply the casting yarns 14 according to the method described above, the injured body portion 10 is positioned in the center of the braiding rings 40, and the free ends of the casting yarns 14 are secured at one end of the injured body portion 10. The carriers 36 are driven around the undulating track of the track plate 34 by the carrier drive motor, thus braiding the casting yarns 14 under-and-over one another, and around the injured body portion 10. The braiding head 26 is simultaneously traversed along the length of the body portion 10 by means of the traversing motor 28, to apply a braided layer of casting yarns 14 over the length of the body portion 10. The braiding head 26 may be traversed back-and-forth several times to deposit several layers of casting yarn 14, depending on the thickness and strength desired for the subject cast. The speed at which the braiding head traverses along the body portion also determines the density of the braid, or in other words, the openness of the weave of the braid. A slow traversing speed produces a dense braid, and a quick traversing speed produces a more open braid.

There are several different braiding architectures which are available which utilize different numbers of strands of yarn, and which form different patterns of under-and-over braiding, however, as previously indicated, the preferred braiding architecture is a "maypole" braiding technique, as opposed to other rotary braiding techniques. The tension applied to the casting yarns 14 during braiding can be varied to produce the desired tightness of the braid. A loosely braided cast will have moderate strength, and increased breatheability, and a tightly braided cast will have increased strength, and decreased breatheability.

The process of braiding the casting materials around an injured body portion with the braiding machine is quick and efficient, and is virtually painless for the patient, and can be performed right in the physician's office if he has the braiding apparatus. The braided casting method eliminates the labor intensive process of manually applying casting materials, and provides a better quality, lighter weight, and stronger cast.

It is seen therefore that the casting method of the instant invention provides an effective method for braiding an orthopedic cast, in situ, around an injured body portion. The braided cast is simple in structure, and since braiding is a combination of weaving and filament winding, it maintains both strength and flexibility, and is effective for all types of casting applications. Braided fibers are mechanically locked for superior strength, and because of its woven structure, braiding can deal more effectively with the complex surfaces of various body portions. Hence, for these reasons, it is seen that the casting method of the instant invention represents a significant advancement in the medical casting art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method of applying an orthopedic cast to an injured body portion, comprising the steps of:
    applying a protective stocking over said injured body portion;
    braiding a plurality of fibrous casting yarns, in situ, over said stocking and around said injured body portion to form a tubular braided cast that closely conforms to the contour of said injured body portion; and
    coating said braided cast with a resinous matrix material, which provides structural rigidity to said cast yet allows said cast to breathe.

2. The method as in claim 1, wherein the step of braiding said cast further comprises the steps of:
    providing a composite braiding machine capable of producing a tubular braid, said braiding machine comprising a tubular braiding head, means for driving said braiding head, and means for traversing said braiding head back-and-forth along the length of said injured body portion;
    positioning said injured body portion within said tubular braiding head, said injured body portion acting as a mandrel around which said casting yarn is braided;
    securing the free ends of said fibrous casting yarn at one end of said injured body portion; and
    driving said braiding head around said body portion, while simultaneously traversing said braiding head back-and-forth along the length of said body portion, thereby braiding said fibrous casting yarn into a tubular braided cast that closely conforms to the contour of said injured body portion.

3. The method as in claim 2, wherein said braiding machine is of the "maypole" type.

4. The method as in claim 1, wherein said fibrous casting yarn is taken from the group consisting of fiberglass, polyethylene, polypropylene, aramid, nylon, polyester, glass, and carbon.

5. The method as in claim 1, wherein said fibrous casting yarn is a yarn taken from the group consisting of multi-filament yarn, multi-filament tow, twisted filament yarn, plied yarn, and twisted staple yarn.

6. The method as in claim 1, wherein said resinous matrix material is a thermoplastic resin.

7. The method as in claim 1, wherein said resinous matrix material is a thermoset resin.

8. The method as in claim 1, wherein said resinous matrix material is a material taken from the group consisting of polyethylene, polypropylene, acrylic, and polyurethane.

9. The method as in claim 1, wherein said matrix material is a ceramic material.

10. The method as in claim 9, wherein said ceramic material is plaster of paris.

11. The method as in claim 1, wherein said fibrous casting yarn includes a pre-impregnated resinous matrix material, said matrix material being activated to provide the aforesaid structural rigidity after said casting yarn is braided onto said injured body portion.

12. The method as in claim 1, wherein said tubular braid is applied back-and-forth over said injured body part for a predetermined distance so as to result in a multi-layer braided cast.

* * * * *